United States Patent [19]

Orevi et al.

[11] Patent Number: 5,246,715
[45] Date of Patent: Sep. 21, 1993

[54] PLATELET-AGGREGATING INHIBITORY AGENTS FROM LEECH SALIVA AND PHARMACEUTICAL PREPARATIONS CONTAINING THE SAME

[75] Inventors: Miriam Orevi; Meir Rigbi; Amiram Eldor, all of Jerusalem, Israel

[73] Assignee: Yissum Research Development Company of the Hebrew University of Jerusalem, Israel

[21] Appl. No.: 368,880

[22] Filed: Jun. 20, 1989

[30] Foreign Application Priority Data

Jun. 24, 1988 [IL] Israel ..................................... 86857

[51] Int. Cl.$^5$ ........................................... A61K 35/57
[52] U.S. Cl. .................................. 424/550; 424/520; 530/855
[58] Field of Search ................. 424/520, 550; 530/855

[56] References Cited

PUBLICATIONS

Baskova, I. P.; Nikonov, G. I., "Antithrombotic effect of salivary gland secretion and of other preparations from *Hirudo medicinalis* after intravenous and peroral administrations into rats.", *Chemical Abstracts*, 106 (No. 9): 39, Abstract No. 60996w (Mar. 2, 1987) and *Vopr. Med. Khim.*, 32(6): 90–93 (1986) (Russ.).

Baskova, I. P.; Nikonov, G. I.; Mazurov, A. V.; Misselwitz, F.; Leitin, V. L.; Repin, V. S.; Avdonin, P. V.; Svitina-Ulitina, I. V., "Mechanisms of inhibition of vascular-platelet hemostasis by salivary gland scretion of the medicinal leech *Hirudo medicinalis.*", *Chemical Abstracts*, 107, (No. 23), Abstract No. 211673n (Dec. 7, 1987) and (Biokhimiya (Moscow) 52(9), 1461–8 (1987).

Baskova et al., Folia Haematol., 111, 831–7 (1984).

D. M. F. Cooper and M. Rodbell, Nature, 285:517–518 (1979).

M. L. Steer and A. Wood, J. Biol. Chem., 254:107931–10797 (1979).

Braquet, P. et al., Pharmacol. Rev., 39:97–145 (1987).

Orevi, M. et al., 15th International Congress of Biochemistry, Jerusalem, (abstract 1390) (1991).

Orevi, M. et al., Prostaglandins, 43:483–495 (1992).

"Platelet Aggregation Inhibitors in *Hirudo medicinalis* Leech Saliva: Partial Purification and Characterization by the Effect on Different Platelet Agonists", M. Orevi et al., *Blood*, 70, (No. 5), Suppl. 1, p. 357a (Nov. 1987).

*Primary Examiner*—Douglas W. Robinson
*Assistant Examiner*—Jean C. Witz
*Attorney, Agent, or Firm*—Curtis, Morris & Safford

[57] ABSTRACT

A composition of matter useful as an inhibitor of blood platelet aggregation, for the treatment of various clinical disorders such as thrombotic, inflammatory and immunological disorders. This composition of matter is derived from the saliva of leeches of the Hirudinidae family. The composition contains various components, all having molecular weights lower than 2,000 daltons. The composition has an inhibitory activity against platelet aggregation induced by various aggregating agents, including Platelet Activating Factor-acether (PAF-acether), arachidonic acid, thrombin, ADP and epinephrine.

10 Claims, 12 Drawing Sheets

PLATELET-AGGREGATING INHIBITORY AGENTS FROM LEECH SALIVA AND PHARMACEUTICAL PREPARATIONS CONTAINING THE SAME

BACKGROUND OF THE INVENTION

Within this application several publications are referenced by Arabic numerals within parentheses. Full citations for these references may be found at the end of the specification, immediately preceding the claims. The disclosures of these publications in their entirety are hereby incorporated by reference into this application in order to more fully describe the state of the art to which this invention pertains.

The medicinal leech Hirudo medicinalis has been used for centuries in the treatment of a variety diseases. The use of leeches for bloodletting reached its height in the eighteenth and early nineteenth centuries, and then began to give way to modern medicine. However, just when the leech was about to disappear from medical practice, new therapies using leeches emerged. Plastic surgeons have been using medicinal leeches to remove blood from post-operative occlusions, a procedure that increases the success of tissue transplants, reduction mammoplasty and the surgical re-attachment of amputated extremeties and digits by reducing the frequency of necrosis (1,2).

These new therapies created a major interest in medicinal leeches and efforts are directed at the isolation, characterization and synthesis of biologically active materials of leech saliva. The chemicals secreted in leech saliva, which may responsible for the success of the said operative procedures, are also being explored as possible therapeutic agents against several diseases, including thrombosis and atherosclerosis (3).

It has long been common knowledge that the host's blood continues to flow from the wound for a long time after the leech has ceased to feed. Indeed, it was shown a century ago (4) that extracts of the medicinal leech contain a substance, hirudin, which prevents blood clotting. Hirudin was isolated and characterized as a protein (5). The pharmacological effects of this potent anticoagulant in animals and in man (6, 7, 9) have also been extensively investigated. The advent of recombinant DNA technology opened the way to, and revived interest in the commercial production of hirudin.

Recombinant hirudin has been produced by major pharmaceutical companies and recent studies have shown that it effectively prevents thrombosis in several animal species and in man (9,10). The anticoagulant properties of hirudin are generally attributed to the inhibition of thrombin and consequently the blocking of fibrin formation. The beneficial effect of the medicinal leech of microsurgery, described above, could not, therefore, be due to hirudin, since thrombi in the microcirculation are usually due to platelet aggregation which is not inhibited by hirudin.

Apart from hirudin, saliva of the medicinal leech has been found to contain additional proteins, eglin, hyaluronidase, collagenase and apyrase (11, 12) and, in general, said publications (11, 12) disclose that leech saliva has platelet-aggregation inhibitory activity. Inhibition of platelet aggregation by leech saliva was also described in references (13) and (14). Platelet aggregation inhibitory activity has been found also in the saliva of a number of blood-sucking anthropods, such as the bug Rhodnius prolixus (15) and the tick Ixodes dammini (16).

Platelets have an important role in normal hemostasis amd in clinical disorders associated with thrombosis and atherosclerosis. Although sticky, they do not adhere to the normal intact endothelial surface of the vessel wall. Injury of the vascular endothelium causes rapid adhesion of circulating platelets on subendothelial structures, and soon other platelets from the circulation are activated by platelet-released products, ADP and thromboxane $A_2$ ($TXA_2$), which cause the formation of platelet aggregates on the damaged wall (17). These platelet aggregates are regarded as the primary hemostatic defense mechanism of the body against blood loss. However, under certain pathological conditions, due to loss or perturbation of the vascular endothelial cells which line the lumen of the vessel wall, platelet aggregates may be formed which play a major role in various clinical disorders including cardiovascular diseases, graft rejection, vascular prostheses, artificial cardiac valves and cancer (18). Following attachment to the vessel wall, platelets may release potent mitogens (platelet-derived growth factor—PDGF) contained within their granules which may stimulate the medial smooth muscle cells (SMC) to proliferate and form the primary lesions of atherosclerosis (18). Medial SMC proliferation is also the cause of the late closure of vascular grafts (e.g. coronary entry bypasses).

There are several specific receptors on platelet membranes which are involved in the formation of platelet aggregates. These receptors are activated by different agonists which are present at sites of thrombus formation. These agonists include ADP released from injured erythrocytes, collagen platelet activating factor (PAF—acether) epinephrine and thrombin. Most agonists activate platelets by binding to their specific receptor, a process which leads to hydrolysis of platelet membrane phosphatidylinositol diphosphate by phospholipase C and causes calcium mobilization from the dense tubular system (17).

Platelet activation causes the release of intrinsic substances (ADP, $TXA_2$, serotonin) which amplify the aggregation process and influence the cells of the vessel wall. Platelet activation also initiates the activation of the clotting system which leads to the formation and polymerization of fibrin.

Thus, the observations of the involvement of the platelets in many pathological conditions led to the realization of the therapeutic importance of drugs which inhibit platelet aggregation. The efficacy of anti-aggregating agents such as aspirin or a combination of aspirin and dipyridamole has been demonstrated in patients with myocardial infarction, prosthetic heart valves and vascular grafts and in patients with organ transplants. Other drugs such as sulfinpyrazone and ticlopidine were also shown to have a beneficial effect in certain thromboembolic disorders (17).

However, though many drugs have inhibitory effects on platelet function, none of them inhibit all the mechanism's which are involved in various forms of thrombosis (19).

Aspirin, which is the most popular platelet inhibitor drug, blocks the arachidonate pathway in platelets and can be expected to be effective against thromboembolic events in which $TXA_2$ generation plays a major role, but not if other metabolic pathways predominate, e.g. if thrombin or collagen are the major platelet activator (17). Furthermore dipyridamole, which elevates platelet cAMP levels, has not been shown to have beneficial effects on myocardial infarction when administered alone (17).

Combinations of oral anticoagulants and aspirin have only recently been tested for their antithrombotic efficacy.

Leech saliva obtained by phagostimulation of leeches with ariginine/saline has been shown to inhibit platelet aggregation induced by different agonists (12). Several substances from leech saliva may exert their inhibitory effect. Hirudin, discussed above, inhibits platelet aggregation induced by thrombin, but not by other agonists. Leech collagenase, inhibits collagen-induced aggregation. Leech apyrase inhibits ADP-induced aggregation. Fractionation of lyophilized saliva on Bio-Gel P-2 showed that high molecular weight components inhibited thrombin -, collagen -, and ADP- induced aggregation (12). These inhibitions are apparently due to the presence in this high molecular weight fraction of hirudin, collagenase and apyrase, respectively.

It has now been found that the low molecular weight fractions, obtained by fractionation of lyophilized saliva of the medicinal leech also comprise components which inhibit platelet aggregation, which components are the subject of the present invention.

SUMMARY OF THE INVENTION

The present invention concerns a composition of matter useful as an inhibitor of blood platelet aggregation, for the treatment of various clinical disorders such as thrombotic, inflammatory and immunological disorders. This composition of matter is derived from the saliva of leeches of the Hirudinidae family. This composition of matter comprises various components, all having molecular weights lower than 2,000 daltons. The composition of matter has an inhibitory activity against platelet aggregation induced by various aggregating agents, including Platelet Activating Factor-acether (PAF-acether), arachidonic acid, thrombin, ADP and epinephrine.

In one embodiment of the invention, the composition of matter is derived from *Hirudo medicinalis*. It is obtained by collecting the low molecular weight fractions of the dilute *H.medicinalis* saliva which is chromatographed on Bio-Gel ® P-2 The components of the composition of matter all have a molecular weight which is lower than 2,000 daltons. The fractions of the said composition of matter are hereafter designated as Fractions II, III and IV.

In another embodiment, the invention provides the composition of matter, comprised in Fraction II. This fraction II composition of matter inhibits platelet aggregation induced by PAF-acether and thrombin, has an absorbance at 260 nm twice as high as that at 280 nm, and, as indicated from thin-layer chromatography and HPLC of chloroform-methanol extracts of its active components, may consist of phospholipids.

In still another embodiment, the invention provides the composition of matter comprised in Fraction III. This Fraction III composition of matter inhibits platelet aggregation induced by arachidonic acid, ADP and epinephrine. Inhibition of aggregation induced by arachidonic acid is accompanied by a marked increase in thromboxane formation. The Fraction III composition of matter has absorbances at 260 nm and 280 nm which are almost equal. This fraction also absorbs at 215 nm, which may indicate the presence of a peptide.

In yet another embodiment, the invention provides the composition of matter comprised in Fraction IV. This Fraction IV composition of matter inhibits platelet aggregation induced by arachidonic acid with an accompanying increase in thromboxane formation. The active component is hydrophobic and, as determined by HPLC, consists of several lipid components.

In yet a further embodiment of the invention the composition of matter is derived from the saliva, the salivary glands of the head section of the Nile leech, *Limnatis nilotica,* also of the family Hirudinidae. The saliva inhibits bloods coagulation and platelet aggregation.

The invention is also directed at pharmaceutical preparations which comprise as active components effective amounts of the composition of matter of the invention, of Fraction II composition of matter, of Fraction III composition of matter or of Fraction IV composition of matter, or mixtures thereof, which have platelet aggregation inhibitory activities, in a pharmaceutically acceptable carrier. Pharmaceutical preparations containing any of said active ingredients, together with a high molecular weight component of leech saliva such as. e.g., hirudin, with a pharmaceutically acceptable carrier are also contemplated.

The pharmaceutical preparations of the present invention may be used for treatment of several conditions involving platelet aggregation and also for preventing platelet aggregation. Thus the pharmaceutical preparations of the present invention may be used for the treatment of various thromboembolic disorders, including venous thrombosis and peripheral arterial thrombosis, cerebrovascular thrombosis, miocardial infarction and patients with arterio-venous shunts. The present preparations may also be used for preventing the rejection of allografts (kidney, liver, heart). The preparations of the invention may be used for treatment of various autoimmune disorders, including systemic lupus erythematosus, rheumatoid arthritis and polyarthritis nodosa. Prevention of spread of metastases and treatment of various solid tumors may also be achieved by use of the preparations of the present invention and their use in preservation of artificial organs, cardiac valves and artificial vascular segments is also contemplated.

The preparations according to the invention may be administered orally or parenterally in dosage unit formulations containing conventional non-toxic pharmaceutically acceptable carriers, diluents, adjuvants and vehicles as desired. The term parenteral as used herein includes subcutaneous, intravenous, intraarticular and intratechal injection and infusion techniques. Dosage unit preparations may contain daily required amounts of the purified compositions of matter of the present invention or submultiples thereof to make up the desired dose. The specific therapeutically effective dose level for any particular patient will depend upon a variety of factors including the activity of the specific active material employed, the age, body weight, general health, sex, diet, time of administration, route of administration, rate of excretion, etc.

As used herein, the term "pharmaceutically acceptable carrier" means an inert, non-toxic solid or liquid filler, diluent or encapsulating material, not reacting with the active ingredients according to the invention. These carriers are known to the man versed in the art. Wetting agents and emulsifiers, as well as release agents, coating agents and preservatives can also be present in the preparations of the invention. The amount of active ingredient that may be combined with the carrier materials to produce a single dosage form will vary, depending upon the patient treated and the particular mode of administration.

In addition, the invention provides said pharmaceutical preparations wherein said carrier is a suitable pharmaceutically acceptable gel base or cream base. These preparations may be used for coating, prior to use, indwelling catheters, vascular grafts and artificial organs, which devices are usually made from plastics materials and also from synthetic fabrics like Dacron. Coating said devices with the gel- or cream-based preparations of the invention may be useful in preventing platelet aggregation post insertion.

Methods of inhibiting platelet aggregation, and treating and preventing the said pathological condition by administering to a subject any of the said pharmaceutical preparations are also provided by the present invention.

The compositions of matter, pharmaceutical preparations and methods of the present invention will be better understood by reference to the following experiments, examples and discussion, which are given for purposes of illustration and do not in any way limit the scope of the invention, which is defined by the appended claims.

DESCRIPTION OF THE DRAWINGS

A sample of lyophilized dilute saliva (2.54 mg protein) suspended in 3.0 ml of 0.2M ammonium bicarbonate at pH 7.9 was applied to a 1×50 cm column of Bio-Gel P-2 equilibrated with the same solution. 2 ml fractions were collected at 4° C. and a flow rate of 14.4 ml/h.

A. , A280; , A260; , protein determined by the Lowry method.

B. , arginine content (Sakaguchi) and , conductivity (NaCl). Main fractions are indicated by Roman numerals and alternate light and stippled areas.

A 15% gel was used. A sample of lyophilized fraction I (FIG. 4A) containing 0.3 mg of protein was dissolved in 300 μl sample buffer (10 mM Tris HCl/10% glycerol/3% SDS pH 6.8) with or without 8.5% dithiothreitol (DTT). 60 μl aliquots were run at 30 mA for 30 min. and then at 20 mA for 150 min.

A. Denatured salivary proteins. DTT was added and samples were boiled for 5 min.

B. Native salivary proteins. DTT was not added and samples were not boiled. M. Markers. Numbers are for molecular weights in kilodaltons. The identity of proteins of known molecular weight (17) is suggested by the markers. Clg, collagen; Ap II, apyrase II; Hy, hyaluronidase; Hi2, Hi,hirudin dimer and monomer respectively; Eg, eglin. Markers: Phb, phosphorylase b; BSA, bovine serum albumin; OA, ovalbumin; CA, carbonic anhydrase; STI, soybean trypsin inhibitor; LA, lactabulmin. In Lane A (denatured proteins) the hirudin dimer of Lane B appears to have dissociated into monomer and a new band of molecular weight slightly under 20 kD is formed.

A. Apyrase activity, expressed as millimoles of phosphate ions released from ATP by 1 ml of Bio-Gel eluate per hour.

B. Hirudin. The inset is the calibration curve with U.S. Standard thrombin. For the determination of apyrase and hirudin, see EXPERIMENTAL RESULTS, Materials and Methods.

Aggregating agents and final concentrations were:
A. PAF- acether, 0.1 μM;
B. arachidonic acid, 70 μM;
C. thrombin, 0.1 TU/ml;
D. ADP, 2 μM;
E. epinephrine, 11 μM;
F. collagen, 1.2 μg/ml.

The degree of inhibition is expressed as percent loss of percent aggregation in the absence of inhibitor, i.e. with Hepes buffer mixture replacing eluate fractions (see section "Platelet aggregation tests" hereafter). As may be seen, such calculations showed apparent inhibition between 20 to 40 percent even in the first eluate tubes (between Tubes 1-4) and in the last tubes (Tubes 17-20), all of which only contained eluent which had passed through the column. This level of inhibition is threfore regarded as a "baseline", being inherent in the experiment, and considered as significant is only inhibition greater than the apparent baseline of each aggregating agent. Fraction III contains both peaks of NaCl and arginine (FIG. 4B). Arginine was reported to inhibit platelet aggregation induced by collagen (27) and thrombin (28). This was confirmed with a solution of arginine and NaCl at concentrations equal to those in Fraction III. The effect of Fraction III on aggregation by these agents could not therefore be determined. Roman numerals and alternate light and stippled areas indicate main fractions.

(a) Phosphatidyl choline standard (10 μl)
(b) Sample (Tube 68) (100 μl.
(c) Sample (100 μl) together with Standard (5 μl).

EXPERIMENTAL RESULTS

Materials and Methods

Collection of Dilute Leech Saliva

Figure 1:
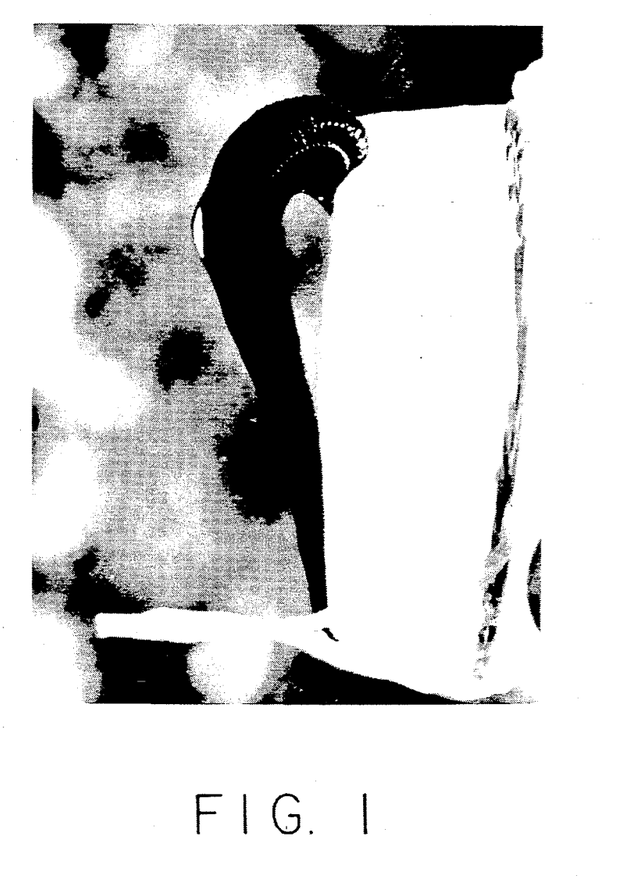
FIG. 1. Leech, prior to feeding, probing the membrane containing above it a stimulant solution of arginine in saline.
Figure 2:
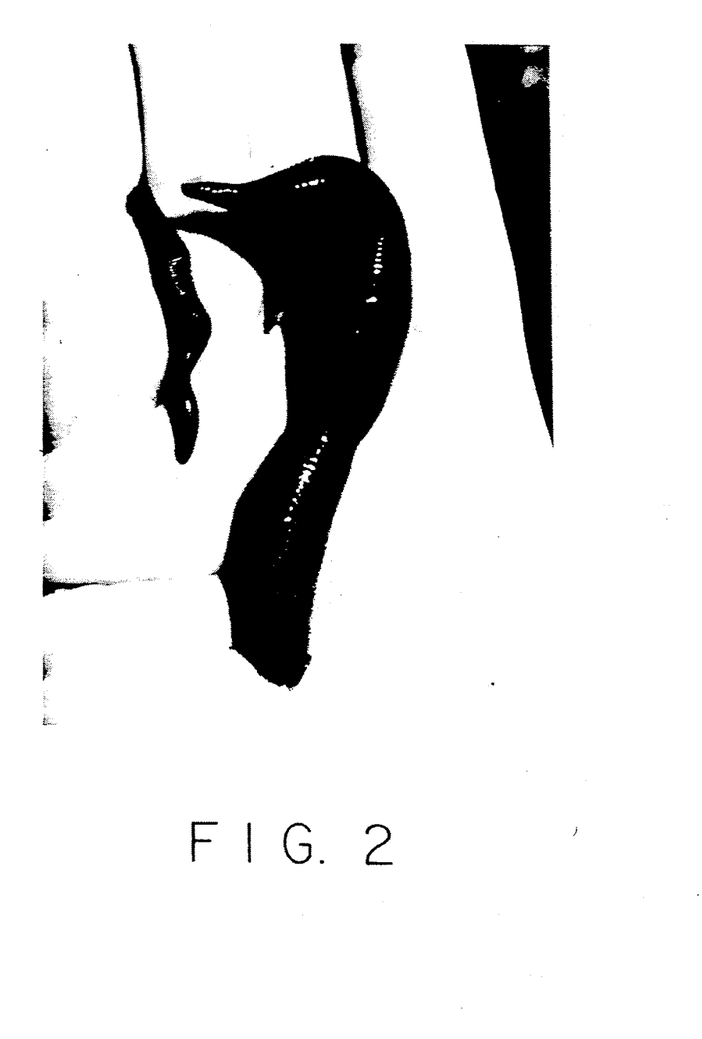
FIG. 2. Two leeches: One before and one after a "meal" of arginine in saline.
Figure 3A:
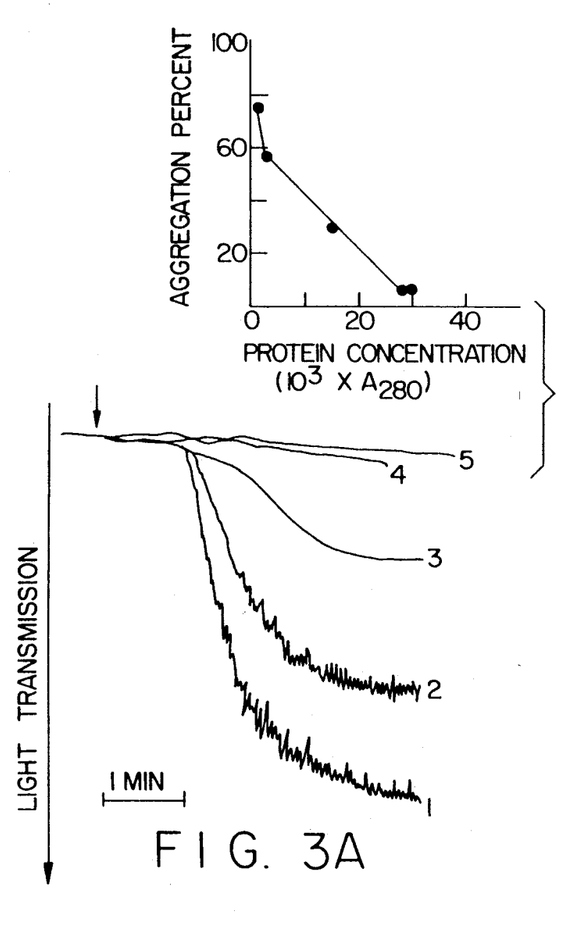
FIG. 3. The effect of H.medicinalis dilute saliva on platelet aggregation induced by (A) collagen; (B) ADP; (C) epinephrine and (D) PAF-acether. Numbers next to tracings indicate the order of increasing volume of saliva. Boxes show percent aggregation as a function of $A_{280}$.
Figure 3B:
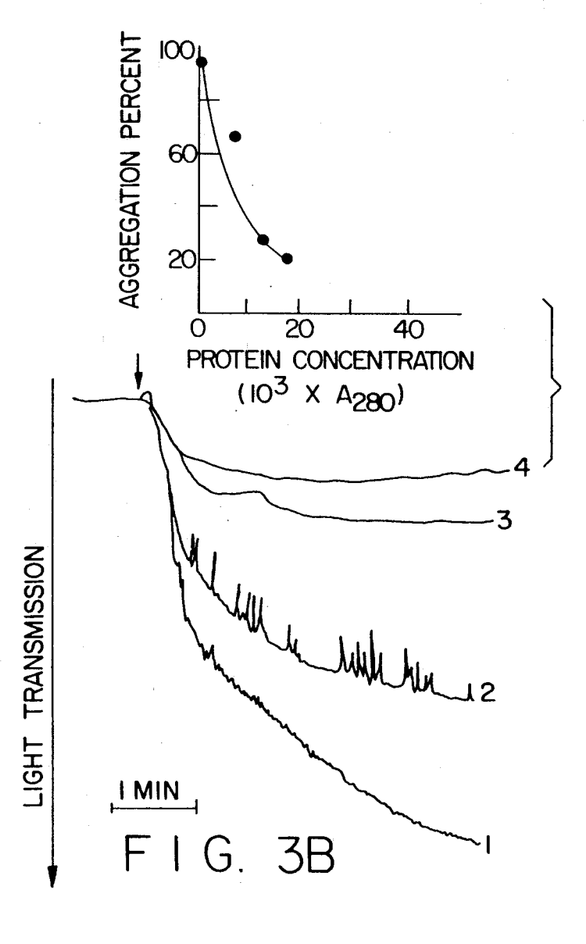
Figure 3C:
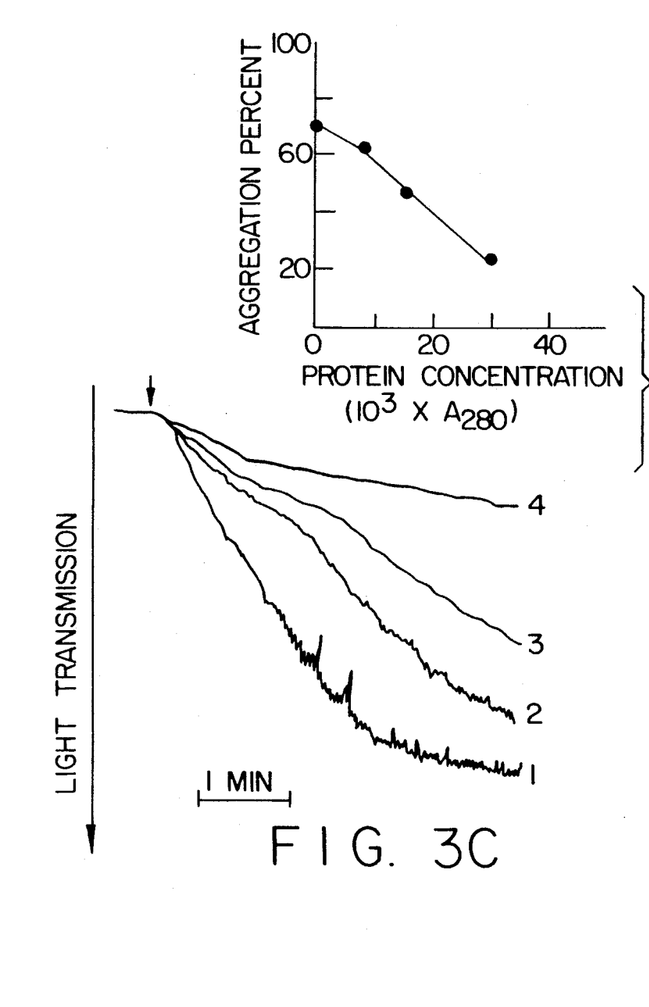
Figure 3D:
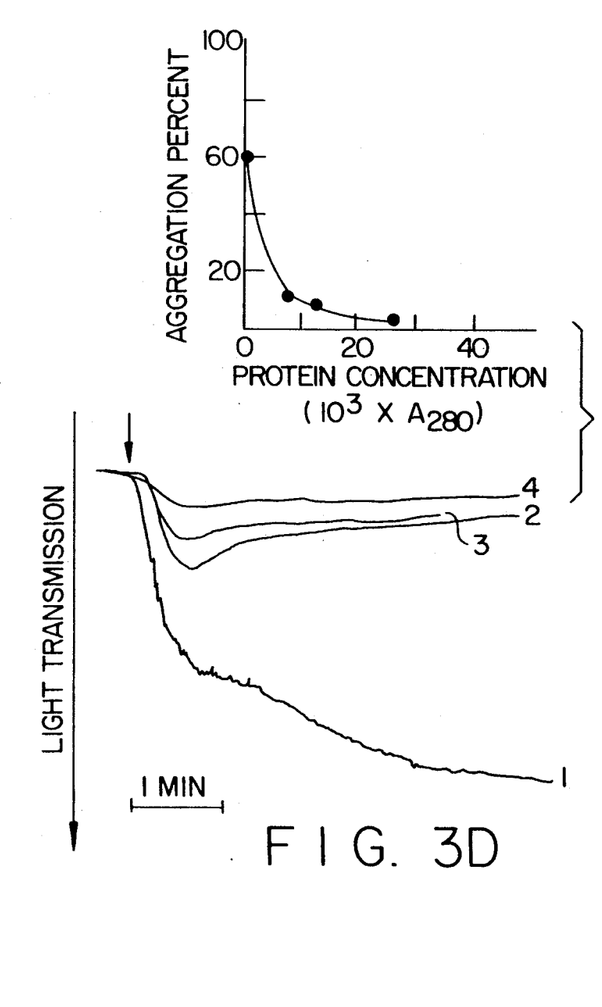

Starved Hirudo medicinalis leeches (Biopharm, Swansea, UK) were placed in a glass container filled with water. The leeches were phagostimulated by a solution of 1 mM arginine hydrochloride in saline, at 37° C., placed over a washed Baudruche membrane (dried calf intestine, Long and Long, Inc., Belleville, N.J.) which had been stretched across the bottom of an open-ended plastic cylinder (FIGS. 1 and 2), immersed in the glass container. Sucking lasted about 20 min. On satiation, the leeches usually dropped from the membrane and sank to the bottom of the container. They were collected, wiped with tissue paper and the swallowed solution containing the secreted saliva was forced out through the mouth by squeezing the leech from the posterior end forwards. Only colourless fluid, herein referred to as dilute saliva, containing no hemoglobin, and therefore, presumably, no other blood components, was used for the experiments. Dilute saliva of about 8–10 leeches was pooled and, if desired, lyophilized. The lyophilizate was dissolved in a small volume of 0.2M ammonium bicarbonate at pH 7.9.

Gel Filtration

A 1×50 cm column of Bio-Gel P-2 (Bio-Rad) was equilibrated with 0.2M ammonium bicarbonate, pH 7.9. The concentrated saliva was applied to the column and was eluted at 4° C. at a flow rate of 14.4 ml/h for desalting and fractionation of components according to their molecular weight. 2 ml fractions were collected and stored at −70° C.

Protein Concentrations

Protein was determined by the method of Lowry et al. (20) and also by absorbance at 280 nm with a Spectronic 2000 spectrophotometer (Bausch and Lomb).

Molecular Weights Determination

Sodium dodecyl sulphate polyacrylamide gel electrophoresis was carried out by the Tris-glycine method of Laemmli (21) with 15% polyacrylamide. Gels were stained with Coomassie Blue. Molecular weights were estimated by reference to the proteins of a Pharmacia LMW calibration kit.

Hirudin Assay

Hirudin was assayed by measuring the inhibition of thrombin activity with the chromogenic substrate D-Phe-L-pipecolyl L-Arg-p-nitroanilide (S2238, Pentapharm, Basel) at pH 7.8 and 25° C. (22). A 1 nM solution of the thrombin used, as determined spectrophotometrically, was equivalent to 0.11 NIH (National Institute of Health) units/ml. 1 Hirudin unit is defined as the amount which inhibits 1 NIH unit of thrombin.

Arginine

Arginine was determined by the method of Sakaguchi (23).

Platelet Rich Plasma

Blood from healthy individuals who had not ingested drugs for at least 10 days before testing was obtained by venipuncture with a two-syringe tenchnique and was mixed with 0.1 volume of 3.2% trisodium citrate. Platelet rich plasma was prepared by centrifugation at 150 g for 10 min. at room temperature. Tubes were kept tightly capped under 5%$CO_2$/95%air until used. The preparations yielded between 1.8 to 4.2×$10^5$ platelets/ml as determined with a Coulter Counter (Coulter Electronics, Hialeah, Fla., U.S.A.).

Platelet poor plasma was prepared by centrifugation of the rich plasma at 1500×g.

Platelet Aggregation Tests

Aggregation tests performed with a dual-channel Payton aggregometer (siliconized cuvettes, constant stirring at 1,000 rpm at 37° C.) (24). Platelet rich plasma (400 μl), HEPES (N-hydroxyethylpiperazine-N-2-ethanesulphonic acid) buffer mixture (0.1M HEPES, 1 mM $MgCl_2$, 1.8 mM $CaCl_2$, 0.15M NaCl, 4 mM KCl and 11 mM glucose; pH 7.35) and test sample (to give 50μl together with aggregating agent) were preincubated in the aggrecorder for 1 min. followed by the addition of aggregating agent.

Aggregating agents and their final concentrations in the text mixture were as follows: ADP (Sigma) 2 μM; collagen (Hormon Chemie, Munich), 1,2 μg/ml; thrombin (Parke, Davis & Co) 0.1 NIH units/ml; epinephrine (Parke, Davis & Co.) 11 μM; PAF-acether (Platelet Activating Factor aceter 1-0-hexadecyl-2-acetyl-glyceryl-3-phosphonylcholine) (Sigma) 0.1 μM; arachidonic acid (Sigma) 70 μM.

Percent aggregation was calculated as the percentage change in light transmission of the full range between platelet rich plasma and platelet poor plasma 4 min. after the addition of the aggregating agent.

Thromboxane $A_2$ ($TXA_2$) Determination

Immediately following the aggregation tests, 0.1 ml samples were taken from the aggregation cuvette and added to 0.9 ml indomethacin solution (10M indomethacin (Sigma) in 0.1M sodium phosphate/0.15M sodium chloride, pH 7.4) to prevent further $TXA_2$ synthesis. Samples were then frozen in liquid nitrogen and stored at −70° C. until assayed for thromboxane $B_2$ ($TXB_2$), the stable product of $TXA_2$. $TXB_2$ was determined by radioimmunoassay as previously described (24). (Anti-$TXB_2$ antibody was kindly provided by Dr. B. B. Wexler, Cornell University, N.Y., N.Y.).

Other specific techniques employed will be described in the description of the experiments.

RESULTS

Inhibition of Platelet Aggregation by Dilute Leech Saliva

The inhibition of platelet aggregation induced by collagen, epinephrine and ADP by the *Hirudo medicinalis* leech saliva was previously reported, and this experiment is prior art (12). The experiment was repeated within the scope of present research and incorporated herein in order to give a more complete description of the art.

Results are illustrated in FIG. 3 which shows the inhibition by dilute leech saliva of aggregation induced by collagen, ADP, epinephrine and PAF-acether and also the decrease in aggregation as a function of saliva concentration as measured by absorbance. Results show the saliva inhibits PAF-induced aggregation much more strongly than the aggregation induced by the other agents tested. As mentioned in the Background of the Invention, leech saliva also strongly inhibits platelet aggregation induced by thrombin and arachidonic acid.

Fractionation of *Hirudo medicinalis* Saliva

Figure 4A:
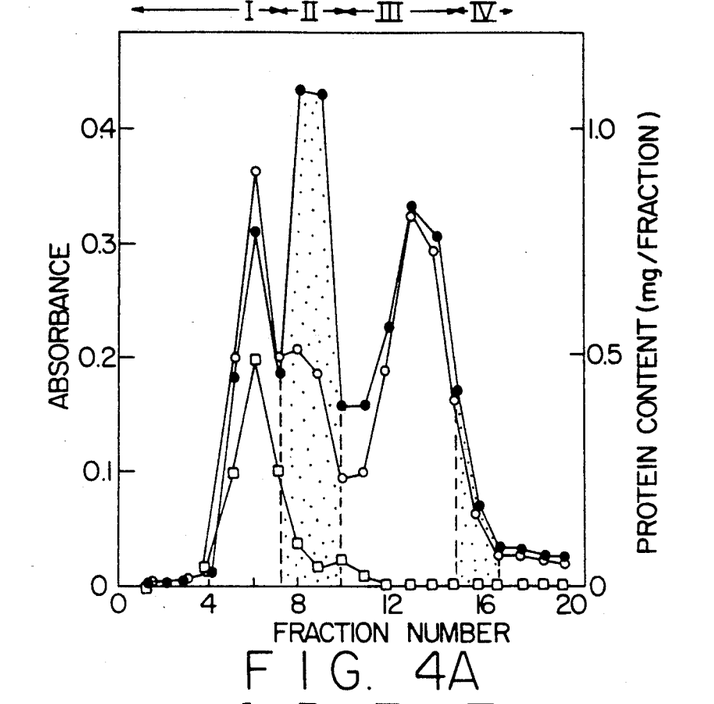
FIG. 4. Elution profile of leech saliva on Bio-Gel P-2.
Figure 4B:
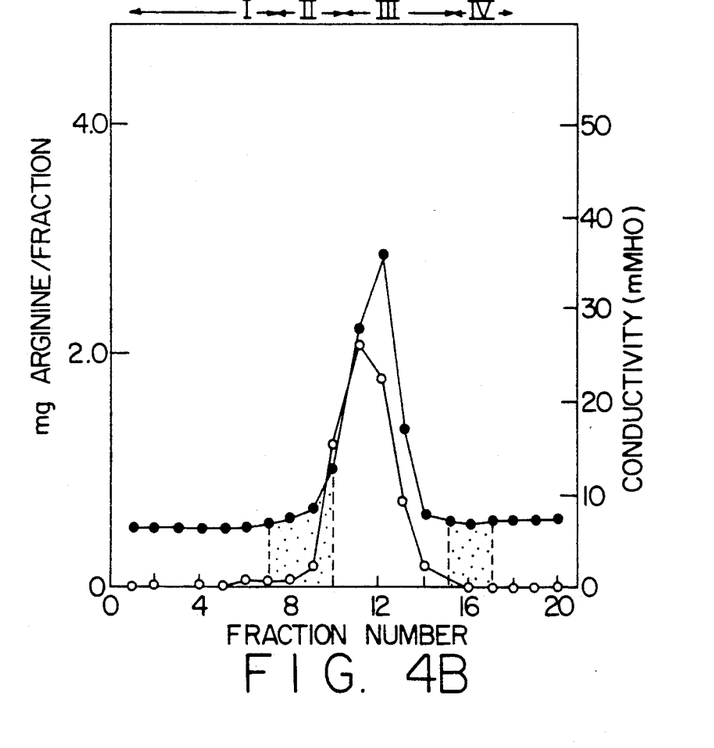

Dilute leech saliva from a *Hirudo medicinalis* leeches (80 ml) was pooled and lyophilized. The lyophilizate was dissolved in 0.2M ammonium bicarbonate, pH 7.9, and was fractioned by gel permeation on Bio-Gel P-2 as described above under Methods. The elution pattern of a typical experiment (one of four) is illustrated in FIG. 4. The 2 ml fractions were then pooled to give four major fractions (I–IV) as follows:

Fraction I (Tubes 4–6). The absorbance at 280 nm was slightly higher than at 260 nm. As seen from the Lowry determination, this fraction contains protein. It is the cut-off fraction of Bio-Gel P-2 containing components of molecular weight greater than 2 kD.

Fraction II (Tubes 8-10). The absorbance at 260 nm was about twice as high as that at 280 nm. Extraction of the active components with chloroform-methanol, thin-layer chromatography and HPLC on a Lichrosorb-60 column indicates that this fraction contains lipids.

A more detailed description of the components of this fraction will be given subsequently. The components of this Fraction II and subsequent fractions eluted beyond the cut-off volume have molecular weights progressively lower than 2 kD.

Fraction III (Tubes 11-14). Absorbances at 260 nm and 280 nm are almost equal. This fraction also absorbs at 215 nm.

Fraction IV (Tubes 15-17). This lower section of the peak of fraction III is marked by the absence of absorbance at 215 nm.

Specificity of Platelet Aggregation Inhibition towards Different Agonists by Bio-Gel P-2 Fractions The inhibitory effect of dilute leech saliva fractions (FIG. 3) on platelet aggregation induced by PAF-acether, arachidonic acid, thrombin, ADP, epinephrine and collagen is shown in FIG. 7. It may be seen in this Figure that the strongest inhibition induced by different agents is to be found in different tubes (fractions).

Figure 6A:
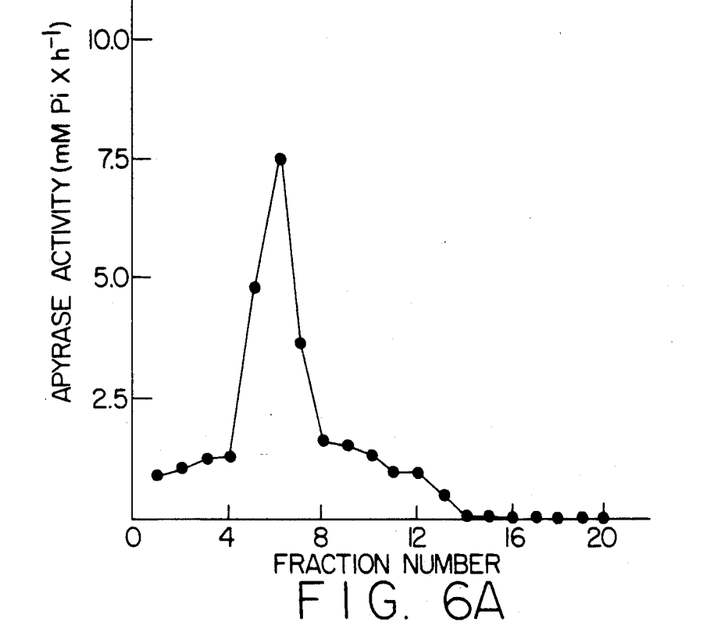
FIG. 6. Apyrase and hirudin activities of DLS fractions eluted from the Bio-Gel column (FIG. 4).
Figure 6B:
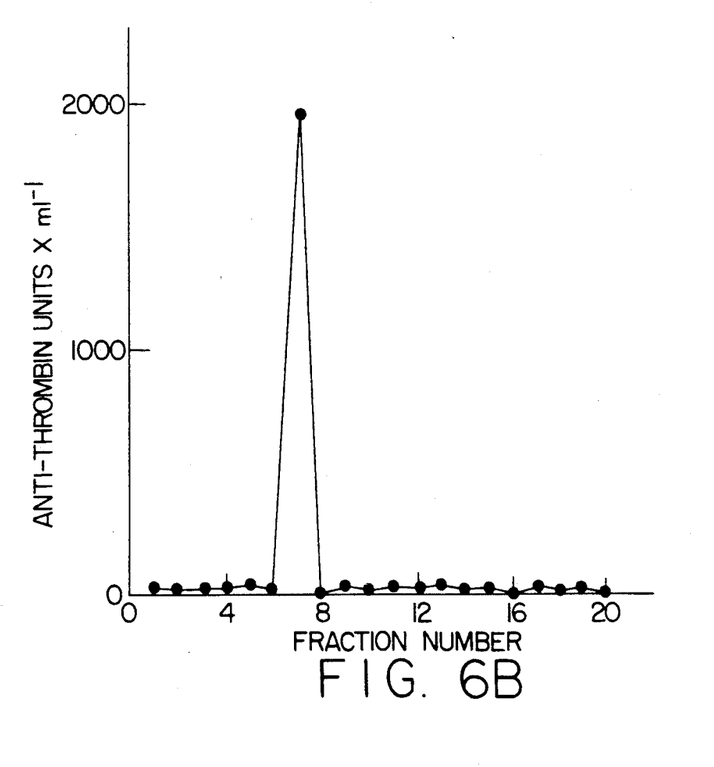
Figure 6C:
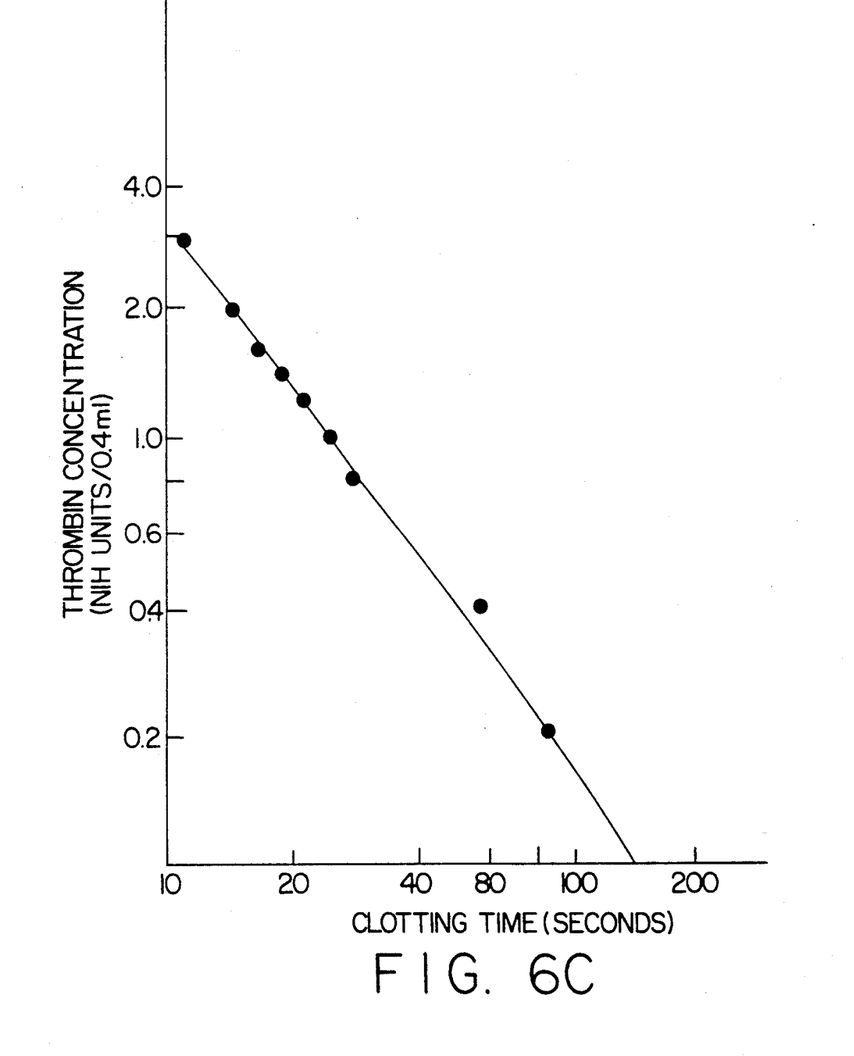
Figure 7A:
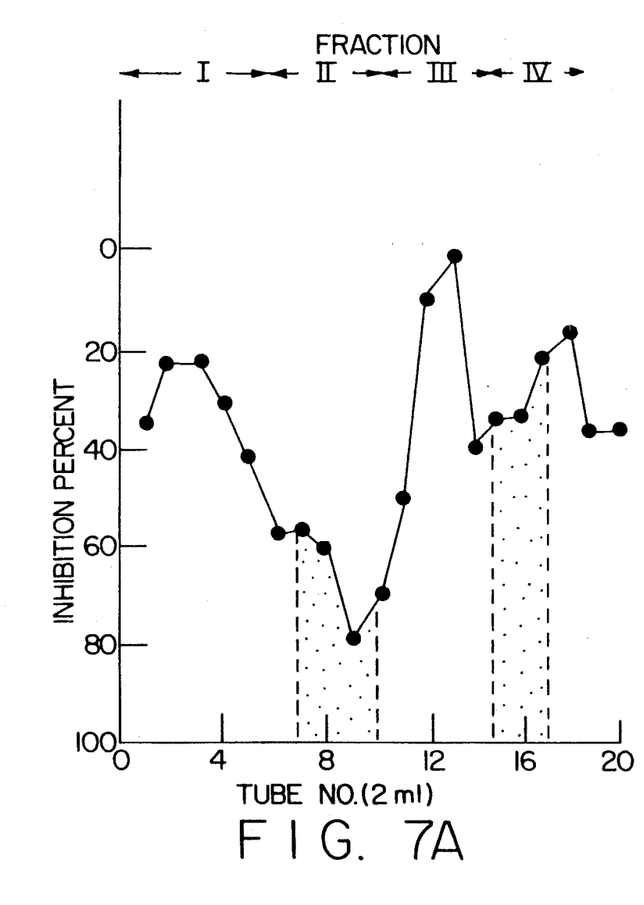
FIG. 7. The inhibition of platelet aggregation by DLS fractions eluted from the Bio-Gel P-2 column (FIG. 4A).
Figure 7B:
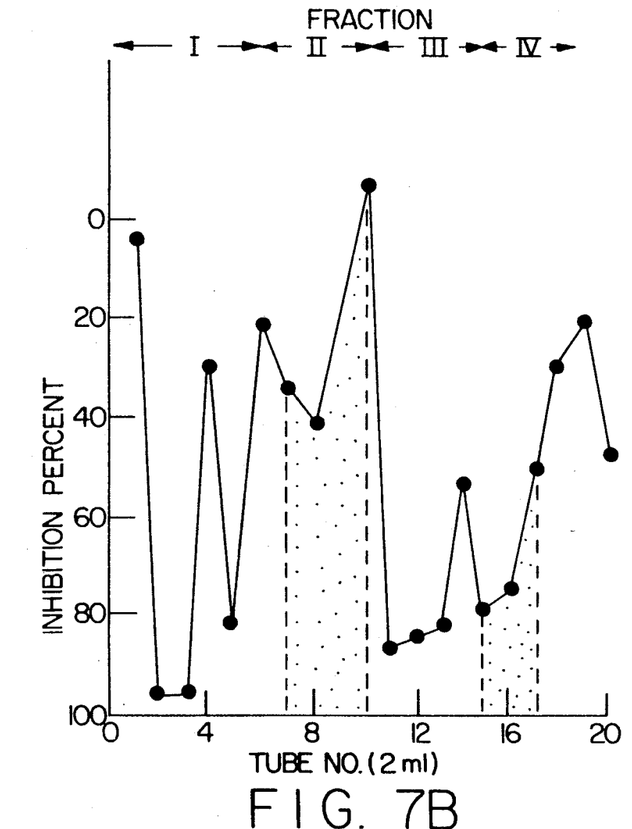
Figure 7C:
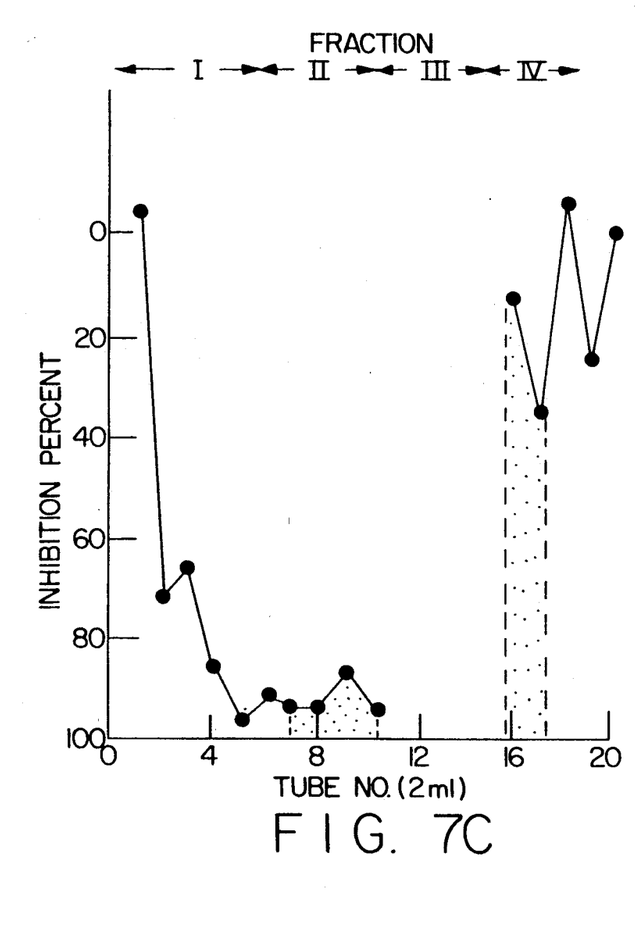
Figure 7D:
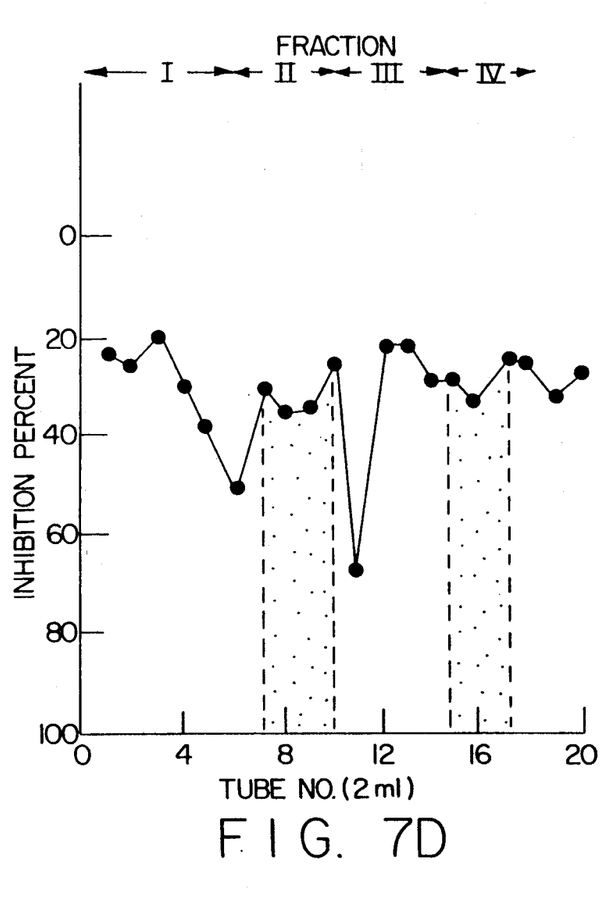
Figure 7E:
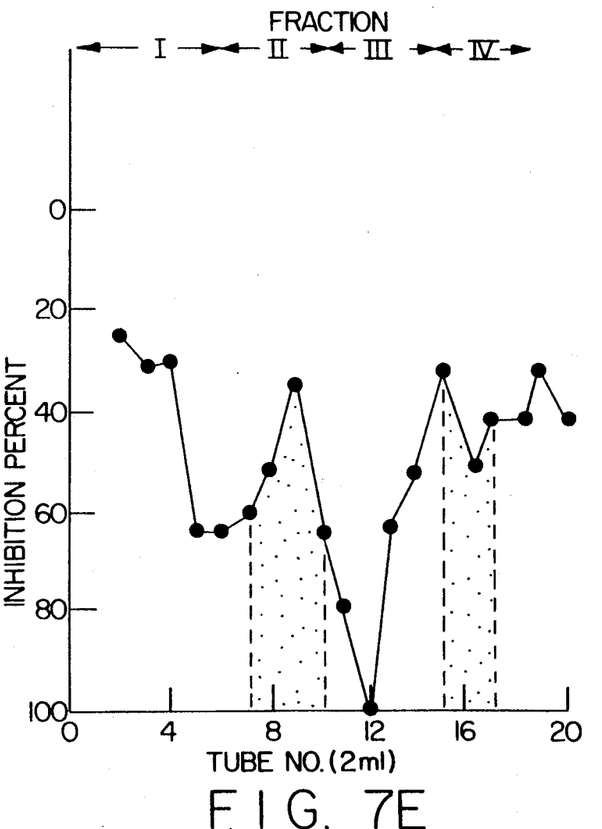
Figure 7F:
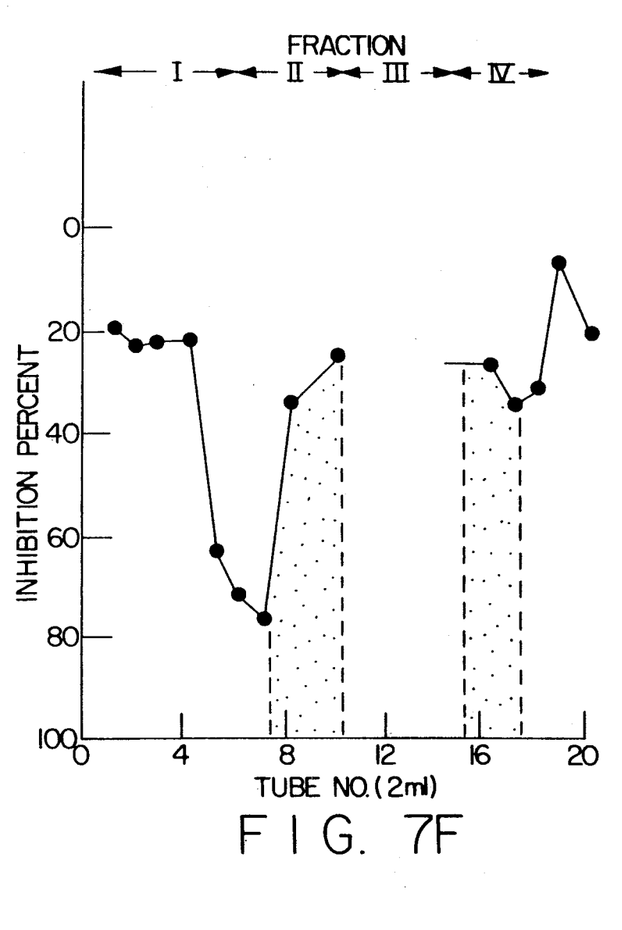

The components of Fraction II strongly inhibit PAF-acether induced aggregation. This inhibitory activity reaches a maximum in Tube 9, beyond which it decreases rapidly. Besides inhibiting PAF-acether induced aggregation, Fraction II inhibited aggregation induced by thrombin. It was established that the inhibition of thrombin-induced aggregation is not due to traces of hirudin from Fraction I, as may be seen from the following data: (a) Thrombin clotting activity was not inhibited (FIG. 6); (b) In another run, with 1×75 cm Bio-Gel P-2 column, and using the more sensitive assay of hirudin, described under Materials and Methods, the early tubes of Fraction II were found to contain 0.6 hirudin units/ml or the equivalent of 0.012 units/ml in the aggregation test, as against 0.128 thrombin by Fractions III and IV was accompanied by a large significant increase in $TXA_2$ production (Table 1).

Extraction of Leech Saliva

Extraction of *H. medicinalis* leech saliva was performed according to the method of Bligh. E. J. and Dyer. H. J. (25). 65 ml of dilute *H. medicinalis* leech saliva ($A_{280}=0.406$) were lyophilized. The lyophilizate was suspended in 2.4 ml double-distilled water, 6 ml methanol and 3 ml chloroform. Additional 3 ml of chloroform and 3 ml of double-distilled water further were added. The upper chloroformic phase was separated, evaporated to dryness and then suspended in 1 ml chloroform. 0.5 ml were then re-evaporated and suspended in 0.475 ml saline and 0.025 ml ethanol containing 0.5 mg BSA (Sigma). 10μ samples of the solution obtained were tested for by inhibition of platelet aggregation by various agonists. Results are summarized in Table 2.

TABLE 2

Inhibition of Aggregation by Saliva Chloroformic Extract
% Aggregation

| Aggregating Agent | 10 μl extract solution | control 1 (no extract no solvents) | control 2 (50 μl solvents, without saliva ext |
|---|---|---|---|
| PAF-acether | 8 | 81 | 68· |
| Epinephrine | 53 | 70 | 72 |
| Thrombin | 0 | 85 | No result |
| ADP | 10 | 65 | 65 |

These results show that the saliva chloroformic extracts markedly inhibit aggregration induced by PAF-acether, thrombin and ADP.

Extraction and HPLC of Fraction II

Dilute *H. medicinalis* saliva was lyophilized. The lyophilizate was taken up in 0.2M ammonium carbonate, pH 7.9 and applied to 2×75 cm column of a Bio-Gel P-2 Fine equilibrated with the same bicarbonate solution used for fractionation. 104 fractions of 2-ml were collected. Tubes 66-72 correspond to Fraction II

TABLE 1

The Effects of Fractions of *H. medicinalis* Saliva on Platelet Aggregation and Thromboxane Release.

| | Control | | Fraction I | | Fraction II | | Fraction III | | Fraction IV | |
|---|---|---|---|---|---|---|---|---|---|---|
| Aggregating Agent | Percent aggregation | $TXB_2$ ng/ml | Percent aggregation | $TXB_2$ ng/ml | Percent aggregation | $TXB_2$ ng/ml | Percent aggregation | $TXB_2$ ng/ml | Percent aggregation | $TXB_2$ ng/ml |
| Arachidonic acid | 54 ± 16 | 75.0 ± 1.5 | 7 ± 6 | 16.1 ± 3.2 | 45 ± 4 | 101 ± 35 | 12 ± 1 | 252 ± 53 | 22 ± 10 | 159 ± 57 |
| Thrombin | 57 ± 10 | 30.8 ± 13.3 | 5 ± 1 | 1.6 ± 1.1 | 6 ± 2 | 1.7 ± 1.4 | ND | ND | 37 ± 16 | 17.6 ± 4.9 |

Three Bio-Gel eluate tubes were selected showing maximum inhibition of aggregation induced by different agonists (see FIG. 6). Controls consisted of the aggregation mixture with late tubes of the Bio-Gel P-2 eluate containing only ammonium bicarbonate to replace saliva fractions. Averages for the tubes are given ± standard deviation. Figures that are significantly different from those of the controls are underlined. Student's t-test was used with P < 0.001. ND, not determina ble (see text or legend to FIG. 6).

Inhibition of Aggregation and Thromboxane A Release

Most agonists activate the arachidonic acid pathway leading to the formation of labile $TXA_2$. The relationship between the inhibition of platelet aggregation and $TXA_2$ production induced by thrombin and by arachidonic acid was compared (Table 1). Inhibition of thrombin induced aggregation was accompanied by a significant reduction in $TXA_2$ synthesis. Inhibition of arachidonic acid aggregation by Fraction I was also accompanied by inhibition of $TXA_2$ Synthesis. However, inhibition of arachidonic acid induced aggregation of the previous experiments. Fraction II was extracted with chloroform/methanol and the extract was shown to inhibit platelet aggregation induced by PAF-acether.

The contents of Tube 68 (Fraction II) were subjected to HPLC.

HPLC was performed with a 4×250mm column, Lichrosorb SI 60. A gradient of A [hexane: 2-propanol:-$H_2O$ (6:8:0.75)] with B [hexane: 2-propanol: $H_2O$ (6:8:1.4)] was used for column elution.

Each run lasted 60 min.

Results are illustrated in FIG. 8.

Figure 8A:
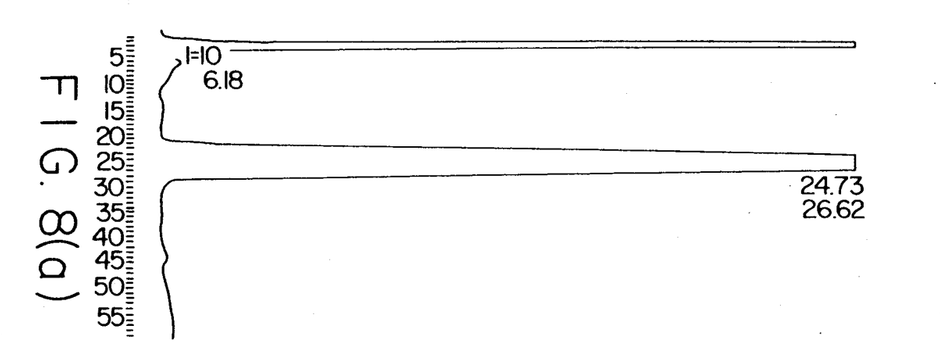
FIG. 8. HPLC of Fraction II (Tube 68 of Bio-Gel chromatography on a 2×75 cm column (elution profile not shown)).

FIG. 8a illustrates a run of phosphatidyl choline (Sigma) standard. A 10 μl sample was injected. The peaks appeared at 24.73 min to 26.82 min.

Figure 8B:
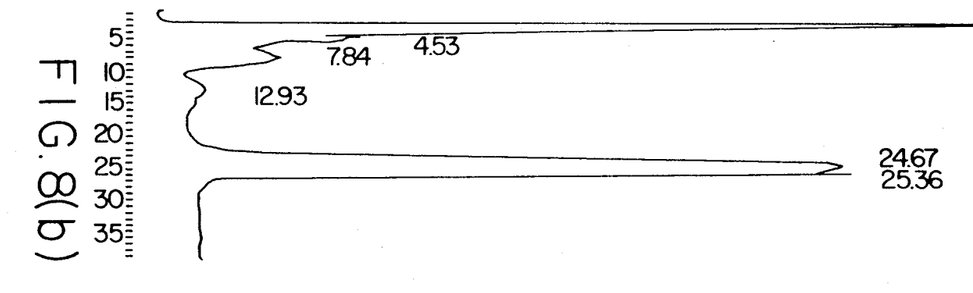

FIG. 8b illustrates a run of 100 μl sample from tube 68 of the eluate from Bio-Gel P-2 (Fine). Peaks appeared at 24.57 to 25.56 min.

Figure 8C:
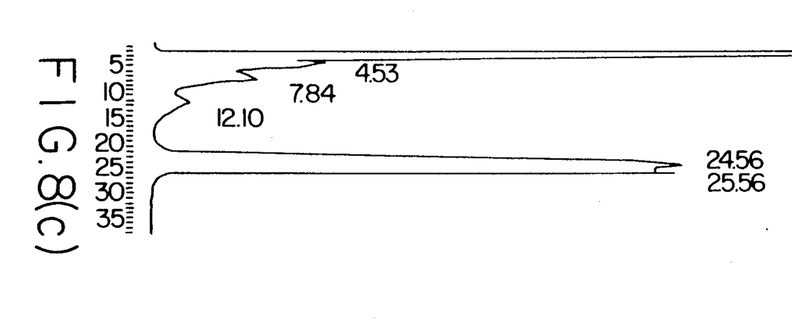

FIG. 8c illustrates a run of a mixture of 5μl mixed phosphatidyl cholines standard with 100 μl sample from Tube 68. Peaks appeared at 24.56 to 25.56 min.

Since the two peaks (of the phosphatidyl choline standard and the tube 68 sample) were co-eluted, it is suggested that Tube 68 contains a phospholipid.

Experiments with the Leech *Limnatis nilotica*

Preliminary experiments were performed with saliva of the leech *Limnatis nilotica*. Saliva was obtained in a manner similar to that described for the *H. medicinalis* and the dilute saliva was pooled and tested for inhibition of platelet aggregation induced by various agents.

Results are summarized in Table 3.

TABLE 3

| Agonist | % Aggregation Volume of Sample | | | |
|---|---|---|---|---|
|  | 3 μl | 5 μl | 50 μl | Control |
| ADP | 45% | 36% | ND | 86% |
| PAF-acether | 44% | 39% | ND | 86% |
| Epinephrine | 45% | 32% | 0 | 72% |

ND Not determined

DISCUSSION

A wide range of high molecular weight and low molecular weight (LMW) inhibitors of platelet aggregation induced by collagen, thrombin, ADP, epinephrine, PAf acether and arachidonic acid were found in leech saliva. The protein fraction (Fraction I), which has been shown to contain apyrase, collagenase, hyaluronidase, hirudin and eglin (11, 12) inhibits coagulation and platelet aggregation induced by all the aggregating agents tested, with the possible exception of PAF-acether. Hirudin acts an an anticoagulant, and inhibits platelet aggregation by binding to thrombin. Hirudin has no inhibitory effect on aggregation induced by any other agonist. The inhibition of ADP and epinephrine induced aggregation is probably due to the presence of apyrase in this fraction. It has previously been shown that potato apyrase inhibits both ADP- (27) and epinephrine-induced platelet aggregation (28).

Figure 5:
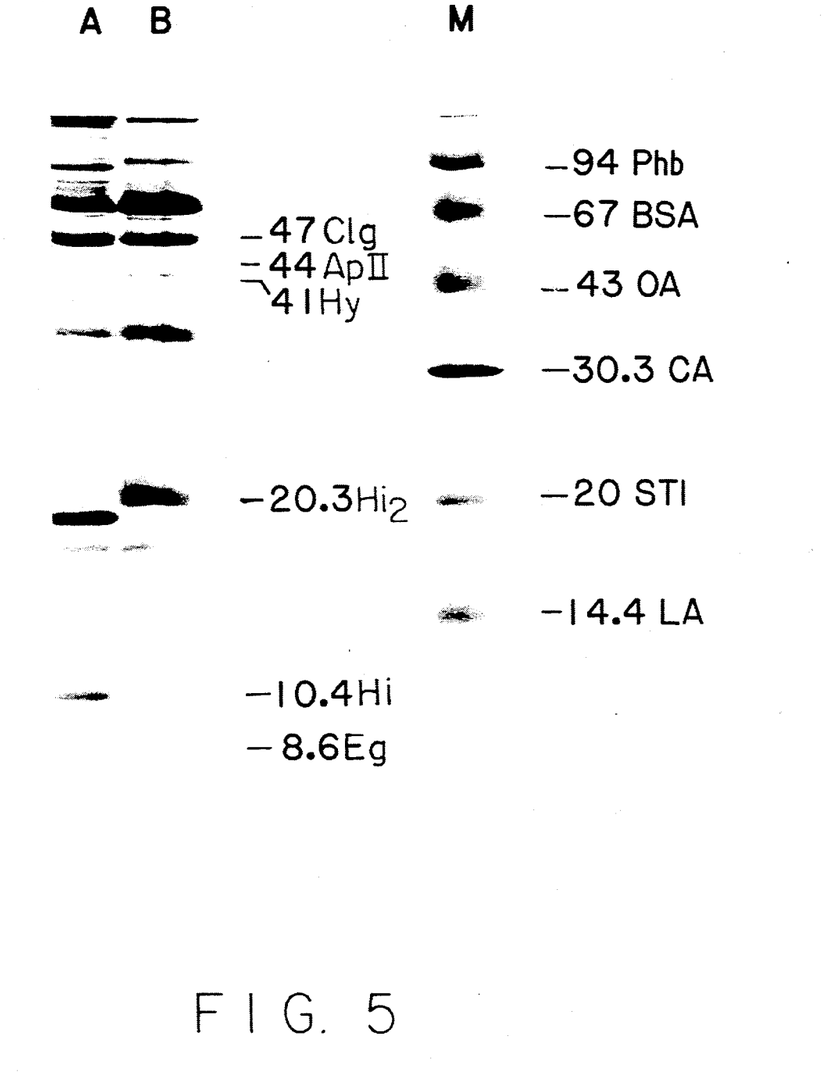
FIG. 5. SDS polyacrylamide gel electrophoresis of leech salivary proteins.

Likewise, the inhibition of collagen-induced aggregation is probably due to interaction of collagen with leech collagenase. Though hydrolysis by the enzyme of the susceptible bonds in collagen is slow, binding may be fast, and this may explain inhibition. That leech saliva contains at least four proteins besides those identified may be seen from FIG. 5. Their biological properties are unknown. It is possible that some of these adsorb lipids, which may explain the inhibition of arachidonic acid induced aggregation by Fraction I.

The LMW fractions, here described for the first time, were found to inhibit platelet aggregation induced by all the aggregating agents tested with the exception of collagen. They differ in specificity of inhibition (FIG. 7) as follows: Aggregation by the powerful PAF acether, which is active at concentrations as low as $10^{-11}$M (29), is strongly inhibited by a lipid component of Fraction II and by no other LMW fraction. A component of LMW Fraction II also inhibits thrombin-induced aggregation, an inhibition which appears not to be due to traces of hirudin. This inhibitor could be extracted into chloroform and had no effect on thrombin clotting activity. Fraction III inhibits aggregation induced by epinephrine, ADP and arachidonic acid. Arachidonic acid induced-aggregation is also inhibited by Fraction IV. Epinephrine and ADP are thought to stimulate platelet aggregation by inhibiting adenylate cyclase via platelet surface receptors (30,31). Leech saliva has been reported to increase the activity of adenylate cyclase, and it was suggested that this is due to the presence of prostacyclin (14). Small quantities of prostacyclin (125 pg/1 ml DLS) were also found by us in fresh samples of dilute leech saliva. However leech saliva which was allowed to stand at room temperature for two hours retained full antiaggregatory activity. Hence the inhibition of platelet aggregation induced by ADP and epinephrine could not be due to prostacyclin which is destroyed under these conditions. Other prostaglandins ($E_1$ and $D_2$) which inhibit platelet aggregation were not detected in leech saliva (13).

The inhibition by Fractions III and IV of arachidonic acid aggregation was accompanied by an increase in $TXA_2$ production. Generally, inhibition of platelet aggregation is accompanied by inhibition of $TXA_2$ synthesis, as shown with Fractions I and II which inhibited thrombin induced aggregation and Fraction I which inhibited arachidonic acid aggregation (Table 1). The finding that arachidonic acid aggregation was inhibited by Fractions III and IV while $TXA_2$ synthesis was not inhibited suggests that these fractions contain components which block the $TXA_2$ receptor. A similar phenomenon is shown with the synthetic thromboxane analogue, 9-homo-9,11-epoxy-5,13-prostadienoic acid (SQ26,536), which acts as an antagonist of the platelet $TXA_2$ receptor without inhibiting $TXA_2$ synthesis while its 15-R epimer (SQ 26,538) turned out to enhance arachidonic acid oxidation to $TXA_2$ (33). Presumably, the active components of Fractions III and IV block the $TXA_2$ receptor and also stimulate $TXA_2$ synthesis. Aggregation may therefore be inhibited either by the inhibition of thromboxane synthesis, or by the blocking of the thromboxane receptor or both. Leech saliva seems to contain specific components belonging to both these categories.

In the early stages of their formation, thromboembolic occlusions consist mainly of platelet aggregates. Platelet aggregation is induced by a wide range of agents. Hence, a range of matching inhibitors is required in order to prevent aggregation effectively. Such a range, we have shown, is present in the saliva of the medicinal leech. We are currently investigating the LMW inhibitors, some of which may turn out to be new compounds. The knowledge gained may prove to be valuable in the treatment of thromboembolic disorders and cardiovascular diseases. The present inhibitors appear to be selective, and being of low molecular weight are not liable to generate an immune response, and may thus be useful in treatment of the various clinical disorders described herein.

LIST OF REFERENCES

1. Henderson, H. P., Matli, B., Laring, A. G. Morelli, S. and Sully, L. (1983) *Brit. J. Plastic Surg.* 36, 235.
2. Whitlock, M. R., O'Hare, P. M., Sanders, R. and Morrow, N. C. (1983 *Brit. J. Plastic Surg.* 36, 240
3. Lent, C. (1986) *Nature*, 323, 494.
4. Haycraft, J. B. (1884) *Proc. R. Soc. B* 36, 478.

5. Markwardt, F. (1955) *Naturwissenschaften* 42, 587; (1956 *Arch. Expt. Pathol Pharmakol* 229, 389; (1957) *Hope-Seylers Z. Physiol. Chemie*, 308, 147. Quoted from Markwardt, F. (1970) (*Methods Enzymol.* (G. E. Perlman and L. Lorand, eds.) Vol. XIX, 924.
6. Walsmann, P. and Markwardt, F. (1981) *Pharmazie*, 36, 653.
7. Markwardt, F., Hauptmann, J. Klessen, Ch. and Walsmann, P. (1982) *Thromb. Haemostas.* 47, 226.
8. Markwardt, F., Nowak, G., Sturtzbecher, J. Griessbach, U., Walsmann, P. and Vogel, G. (1984) *Thromb. Haemostas.* 52, 160.
9. *Thromb. Res.* Abstracts of Satellite Symposia XIth International Congr. Thromb Haemostas. Suppl. VII. (H. R. Lijnen, M. Verstraete, eds.).
10. Newer Strategies in the Management of Thrombotic Disorders. Abstracts, Nov. 12-14, 1987, Oak Brook, Ill. 60153, U.S.A. (Loyola University, Chicago).
11. Rigbi, M. Levy, H., Iraqi, F., Teitelbaum, M., Orevi, M., Alajoutsijarvi, A., Horovitz, A., Galun, R., *Comp. Biochem, Physiol.* 1987, 87B:567-573.
12. Rigbi, M., Levy, H., Eldor, A., Iraqi, F. Teitelbaum, M., Orevi, M., Horovitz, A., Galun, R., *Comp. Biochem Physiol* 1987, 88C:95-98.
13. Baskova, I. P. Misselwitz, F., Nikonov, G. I., Novikov, I. D., Levin, V. L. Repin, V. S.: Byul, Eksp. Biol. Meditsin, 97 (696-699). English translation 1984 by Plenum Press.
14. Baskova, I. P. Nikonov, G. I., Khalil, S., Mazorov, A. V., Misselwitz, F., Leitin, V. L., Repin, V. S., Svitina-Ulitina, I. V., Avdonin, P. A., Tkocchuk, V. A., *Thromb Haemostas* 1985, Abstracts_54(1):_18-6_P 1098.
15. Ribeiro, J. M. C. and Garcia, E. S. (1981) *Experientia* 37, 384.
16. Ribeiro, J. M. C., Makoul, G. T., Levine, J. Robinson, D. R. and Spielman, A. (1985) *J. Exp. Med.* 6, 332.
17. Fuster, V., Bradimon, L., Badimon, J., Adams, P. C. Turitto, Chesebro, J. H. (1987) in "Thrombosis and Haemostasis" (M. Verstraete, J. Vermylen, H. R. Lijnen and J. Arnout, eds.) Intl. Soc. Thrombosis and Haemostasis and Leuven University Press, Leuven, pp. 349.
18. Ross. R. (980) *N. Engl. J. Med.* 34, 488.
19. Dodt. J., Seemuller, U., Maschler, R. and Fritz, H. *Biol. Chem. Hoppe-Seyler* (1985), 366, 379.
20. Lowry, O. H., Rosebrough, N. H., Farr, A. L., Randall, R. J. *J. Biol. Chem* 1951, 193:265-275.
21. Laemmli, U. K., T. *Nature* (London), 1970, 227:680-685.
22. Lottenberg, R., J. A., Blinder, M., Binder. E. P., Jackson, C. M. *Biochem. Biophys. Acta,* 1983, 742:539-557.
23. Weber, C. J., *J. Biol. Chem.* 1930, 86:217.
24. Eldor, A., Polliack, G., Voldavsky, I. and Levy M. *Thromb. Haemostas* 1983, 48:132-137.
25. Bligh, E. G., and Dyer, H. J., Can, F. *Biochem, Physiol.* 37, 911-917 (1959).
26. Anderson, E. R., Au-Young, Y-K., Foulks, J. G. *Thromb. Haemostas.* 1983, 49(3): 176-181.
27. Haslam R. J.: Johnson S. A. and Seegers W. H. (eds): Physiology of Hemostasis and Thrombosis. Charles C. Thomas, Springfield,_Ill._1967_p88.
28. Figures W. R., Scearce L. M., Watchfogel Y., Chen J. Colman R. F., Colman R. W. *J. Biol.* 1986 Chem 261:5981.
29. Hanahan D. J.: *Ann Rev. Biochem* 1986 55:483.
30. Mills C. B., Colman R. F., Figures W. R., Morinelli T. A., Niewiarowski S. Colman R. W.: *Fed. Proc.* 1980 39: 1619(a).
31. Jakobs K. H., Saur W., Schultz G.: J. Cyclic Nucleotides Res. 1976 2:381.
32. MacIntyre D. E.: in Gordon J. L. (ed): Platelets in Biology and Pathology Elsevier 1951 211.
33. Harris D. M., Phillips M. B., Michel I. M., Goldenberg H. J., Heikes J. E., Sprague P. W., Antonaccio M. J., Specific stable agonist (SQ 26,538) and antagonist (SQ 26,5361) *Prostaglandins* 1981 22:295.

We claim:

1. A composition effective as an inhibitor of blood platelet aggregation, comprising an isolated fraction derived from Hirudinidae leeches saliva, having absorbance at 260 nm twice as high as its absorbance at 280 nm, wherein active components are phospholipids, all having molecular weights lower than 2,000 daltons and having inhibitory activity against platelet aggregation induced by PAF-acether or thrombin.

2. A composition according to claim 1 derived from saliva of *Hirudo medicinalis* and/or *Limnatis nilotica*.

3. A composition according to claim 1, inhibiting platelet aggregation induced by PAF-acether.

4. A composition according to claim 1, inhibiting platelet aggregation induced by thrombin.

5. A pharmaceutical composition for inhibiting platelet aggregation comprising as active ingredient an effective amount of the composition of matter of claim 1 and a pharmaceutically acceptable carrier.

6. A pharmaceutical composition for inhibiting platelet aggregation comprising as active ingredient an effective amount of the composition of claim 2, and a pharmaceutically acceptable carrier.

7. A pharmaceutical composition according to claim 5 wherein said pharmaceutically acceptable carrier is a pharmaceutically acceptable gel base or cream base.

8. A pharmaceutical composition according to claim 5 wherein the effective amount is an amount effective for the treatment of thrombosis or embolism.

9. A method of inhibiting platelet aggregation comprising administering to a patient in need thereof a therapeutically effective amount of the pharmaceutical compositions of claim 5.

10. A method of treating thromboembolic disorders comprising administering to a patient in need thereof an effective amount of the composition of claim 8.

* * * * *